(12) United States Patent
Yokoi et al.

(10) Patent No.: US 11,008,355 B2
(45) Date of Patent: May 18, 2021

(54) CRYSTAL OF 3'-SIALYLLACTOSE SODIUM SALT N-HYDRATE, AND PROCESS FOR PRODUCING SAME

(71) Applicant: KYOWA HAKKO BIO CO., LTD., Tokyo (JP)

(72) Inventors: Tomoya Yokoi, Tokyo (JP); Hiroshi Nagano, Tokyo (JP); Kikue Mase, Tokyo (JP); Masahiro Abe, Tokyo (JP)

(73) Assignee: KYOWA HAKKO BIO CO., LTD., Tokyo (JP)

( * ) Notice: Subject to any disclaimer, the term of this patent is extended or adjusted under 35 U.S.C. 154(b) by 25 days.

(21) Appl. No.: 16/099,877

(22) PCT Filed: May 8, 2017

(86) PCT No.: PCT/JP2017/017422
§ 371 (c)(1),
(2) Date: Nov. 8, 2018

(87) PCT Pub. No.: WO2017/195743
PCT Pub. Date: Nov. 16, 2017

(65) Prior Publication Data
US 2019/0135846 A1    May 9, 2019

(30) Foreign Application Priority Data
May 9, 2016    (JP) .............................. JP2016-093664

(51) Int. Cl.
*C07H 3/06* (2006.01)
(52) U.S. Cl.
CPC ............ *C07H 3/06* (2013.01); *C07B 2200/13* (2013.01)
(58) Field of Classification Search
CPC .............................. C07H 3/06; C07B 2200/13
See application file for complete search history.

(56) References Cited

U.S. PATENT DOCUMENTS

| | | | |
|---|---|---|---|
| 5,575,916 A | 11/1996 | Brian et al. | |
| 5,714,075 A | 2/1998 | Brian et al. | |
| 9,034,844 B2 * | 5/2015 | Tamerlani ............ | C07H 13/06 514/54 |
| 2012/0071441 A1 | 3/2012 | Tamerlani et al. | |
| 2018/0305388 A1 | 10/2018 | Abe et al. | |

FOREIGN PATENT DOCUMENTS

| | | |
|---|---|---|
| EP | 3378868 A1 | 9/2018 |
| JP | H08-252403 A | 10/1996 |
| JP | H10-513437 A | 12/1998 |
| JP | 2012-522761 A | 9/2012 |
| WO | WO 1998/048817 A1 | 11/1998 |
| WO | WO 2010/116317 A1 * | 10/2010 |
| WO | WO 2017/086443 A1 | 5/2017 |

OTHER PUBLICATIONS

Morissette, S. L. et al., Advanced Drug Delivery Reviews, "High-throughput crystallization: polymorphs, salts, co-crystals and solvates of pharmaceutical solids", 2004, vol. 56, pp. 275-300 (Year: 2004).*
Parente, F. et al., Helicobacter, "Treatment of Helicobacter Pylori Infection Using a Novel Antiadhesion Compound (3'sialyllactose sodium salt). A Double blind, Placebo-Controlled Clinical Study", 2003, vol. 8, No. 4, pp. 252-256 (Year: 2003).*
Vippagunta, S. R. et al., Advanced Drug Delivery Reviews, "Crystalline solids", 2001, vol. 48, pp. 3-26 (Year: 2001).*
Caira, "Crystalline Polymorphism of Organic Compounds," *Topics in Current Chemistry*, 198: 163-208 (1998).
European Patent Office, Extended European Search Report in European Patent Application No. 17796104.2 (dated Nov. 14, 2019).
Endo et al., "Large-scale production of CMP-NeuAc and sialylated oligosaccharides through bacterial coupling," *Appl. Microbiol. Biotechnol.*, 53(3): 257-261 (2000).
Ito et al., "High Stereoselective Glycosylation of Sialic Acid Aided by Stereocontrolling Auxiliaries," *Tetrahedron*, 46(1): 89-102 (1990).
Rencurosi et al., "Human milk oligosaccharides: an enzymatic protection step simplifies the synthesis of 3'- and 6'-O-sialyllactose and their analogues," *Carbohydr. Res.*, 337(6): 473-483 (2002).
Japanese Patent Office, International Search Report in International Patent Application No. PCT/JP2017/017422 (dated Aug. 8, 2017).
Japanese Patent Office, International Preliminary Report on Patentability in Japanese Patent Application No. PCT/JP2017/017422 (dated Nov. 13, 2018).

\* cited by examiner

*Primary Examiner* — Bahar Craigo
(74) *Attorney, Agent, or Firm* — Leydig, Voit & Mayer, Ltd.

(57) ABSTRACT

An object of the present invention is to provide a crystal of 3'-sialyllactose (hereinafter, referred to as 3SL), which is easily handled, and has high storage stability at normal temperature as well as under high temperature conditions, and provide a process for producing the same. The present invention relates to a 3SL sodium salt n-hydrate (wherein n represents any number of 0 to 9, and when n is 0, it is referred to as 3SL sodium salt anhydrate) and a process for producing the same.

15 Claims, 6 Drawing Sheets

CRYSTAL OF 3'-SIALYLLACTOSE SODIUM SALT N-HYDRATE, AND PROCESS FOR PRODUCING SAME

CROSS-REFERENCE TO RELATED APPLICATIONS

This patent application is the U.S. national phase of International Patent Application No. PCT/JP2017/017422, filed May 8, 2017, which claims the benefit of Japanese Patent Application No. 2016-093664, filed on May 9, 2016, which are incorporated by reference in their entireties herein.

TECHNICAL FIELD

The present invention relates to a crystal of 3'-sialyllactose sodium salt n-hydrate (wherein n represents any number of 0 to 9, and when n is 0, it is referred to as 3'-sialyllactose sodium salt anhydrate) which is useful, for example, as a product, a raw material, an intermediate, or the like of health food, pharmaceuticals, cosmetics, and the like, and a process for producing the crystal.

BACKGROUND ART

3'-Sialyllactose [O—(N-acetyl-α-neuraminosyl)-(2→3)-O-β-D-galactopyranosyl-(1→4)-D-Glucose] (hereinafter, referred to as 3SL) is an acidic oligosaccharide in which sialic acid is linked to lactose, and is useful, for example, as a product, a raw material, an intermediate, or the like of health food, pharmaceuticals, cosmetics, and the like.

3SL is one of important oligosaccharides contained in human breast milk and is supposed to have a bioactivity such as a protective activity against infection with a virus or a bacterium, or a growth activity of lactic acid bacterium.

As a method for producing 3SL, a purification method using a gel filtration column (Non-Patent Documents 1 and 2), a simulated moving-bed chromatographic separation device (Patent Document 1), or the like has been disclosed. However, there is no description regarding a method for producing a crystal of 3SL salt. Patent Document 2 describes a method for producing 3SL salt. However, it is not possible to obtain a crystal of 3SL salt with the method.

RELATED ART

Patent Document

Patent Document 1: JP-A-08-252403
Patent Document 2: JP-T-10-513437

Non-Patent Document

Non-Patent Document 1: Carbohydrate Research., Vol. 337, p. 473, 2002
Non-Patent Document 2: Apply Microbiol Biotechnol., Vol. 53, p, 257, 2000

SUMMARY OF THE INVENTION

Problems to be Solved by the Invention

An object of the present invention is to provide a crystal of 3SL, which is easily handled, and has high storage stability at normal temperature as well as under high temperature conditions, and a process for producing the same.

Means for Solving the Problems

The present invention relates to the following (1) to (17).
(1) A crystal of 3'-sialyllactose (hereinafter, referred to as 3SL) sodium salt n-hydrate (wherein n represents any number of 0 to 9, and when n is 0, it is referred to as 3SL sodium salt anhydrate).
(2) The crystal described in (1) above, wherein n is any number of 4 to 9.
(3) The crystal described in (2) above, wherein n is 5.0 or 8.0.
(4) The crystal described in (1) or (2) above, wherein the crystal has peaks at diffraction angles (2θ°) of 7.2±0.2°, 10.9±0.2°, 22.7±0.2°, 21.2±0.2°, and 9.8±0.20 in powder X-ray diffraction.
(5) The crystal described in (4) above, wherein the crystal further has peaks at diffraction angles (2θ°) of 23.3±0.2°, 21.8±0.2°, 17.1±0.2°, 17.8±0.2°, and 24.1±0.2° in powder X-ray diffraction.
(6) The crystal described in (5) above, wherein the crystal further has peaks at diffraction angles (2θ°) of 24.7±0.2°, 16.4±0.2°, 25.6±0.2°, 20.9±0.2°, and 23.9±0.2° in powder X-ray diffraction.
(7) The crystal described in (1) or (2) above, wherein the crystal has the following approximate cell parameters when measured at −173° C. in single crystal X-ray structure analysis: a=11.2942 Å; b=13.3269 Å; c=24.4525 Å; V=3680.5 Å$^3$; and Z=4, and has a space group of P2$_1$2$_1$2$_1$.
(8) The crystal described in (1) above, wherein n is any number which is equal to or greater than 0 and less than 4.
(9) The crystal described in (8) above, wherein n is 1.4, 2.0, or 3.5.
(10) The crystal described in (1) or (8) above, wherein the crystal has peaks at diffraction angles (2θ°) of 8.9±0.2°, 17.1±0.2°, 15.5±0.2°, 19.3±0.2°, and 20.9±0.2° in powder X-ray diffraction.
(11) The crystal described in (10) above, wherein the crystal further has peaks at diffraction angles (2θ°) of 27.4±0.2°, 13.3±0.2°, 22.5±0.2°, 11.8±0.2°, and 23.7±0.2° in powder X-ray diffraction.
(12) The crystal described in (11) above, wherein the crystal further has peaks at diffraction angles (2θ°) of 25.0±0.2°, 10.8±0.2°, 17.9±0.2°, 20.0±0.2°, and 21.8±0.2° in powder X-ray diffraction.
(13) A process for producing the crystal described in any one of (2) to (7) above, comprising a step of precipitating a crystal of 3SL sodium salt n-hydrate by causing a 3SL aqueous solution containing a sodium-containing compound to be left to stand or to be stirred, and a step of collecting the crystal of 3SL sodium salt n-hydrate from the aqueous solution (wherein n has the same meaning as in (2) above).
(14) A process for producing the crystal described in any one of (2) to (7), comprising a step of adding a crystal of 3SL sodium salt n-hydrate as a seed crystal to a 3SL aqueous solution containing a sodium-containing compound, a step of precipitating a crystal of 3SL sodium salt n-hydrate in the aqueous solution, and a step of collecting the crystal of 3SL sodium salt n-hydrate from the aqueous solution (wherein n has the same meaning as in (2) above).
(15) The process described in (14), wherein the step of precipitating the crystal of 3SL sodium salt n-hydrate is a step of precipitating a crystal of 3SL sodium salt n-hydrate by adding or adding dropwise an alcohol solution (wherein n has the same meaning as in (2) above).

(16) The process described in (15), wherein the alcohol solution is a solution selected from the group consisting of C1 to C6 alcohols.

(17) A process for producing the crystal described in any one of (8) to (12), comprising a step of performing forced air drying of the crystal described in any one of (2) to (7) at 45° C. or more for 20 hours or more, or a step of performing vacuum drying of the same at 25° C. or more for 48 hours or more.

MODE FOR CARRYING OUT THE INVENTION

1. Crystal of the Present Invention

Figure 1:
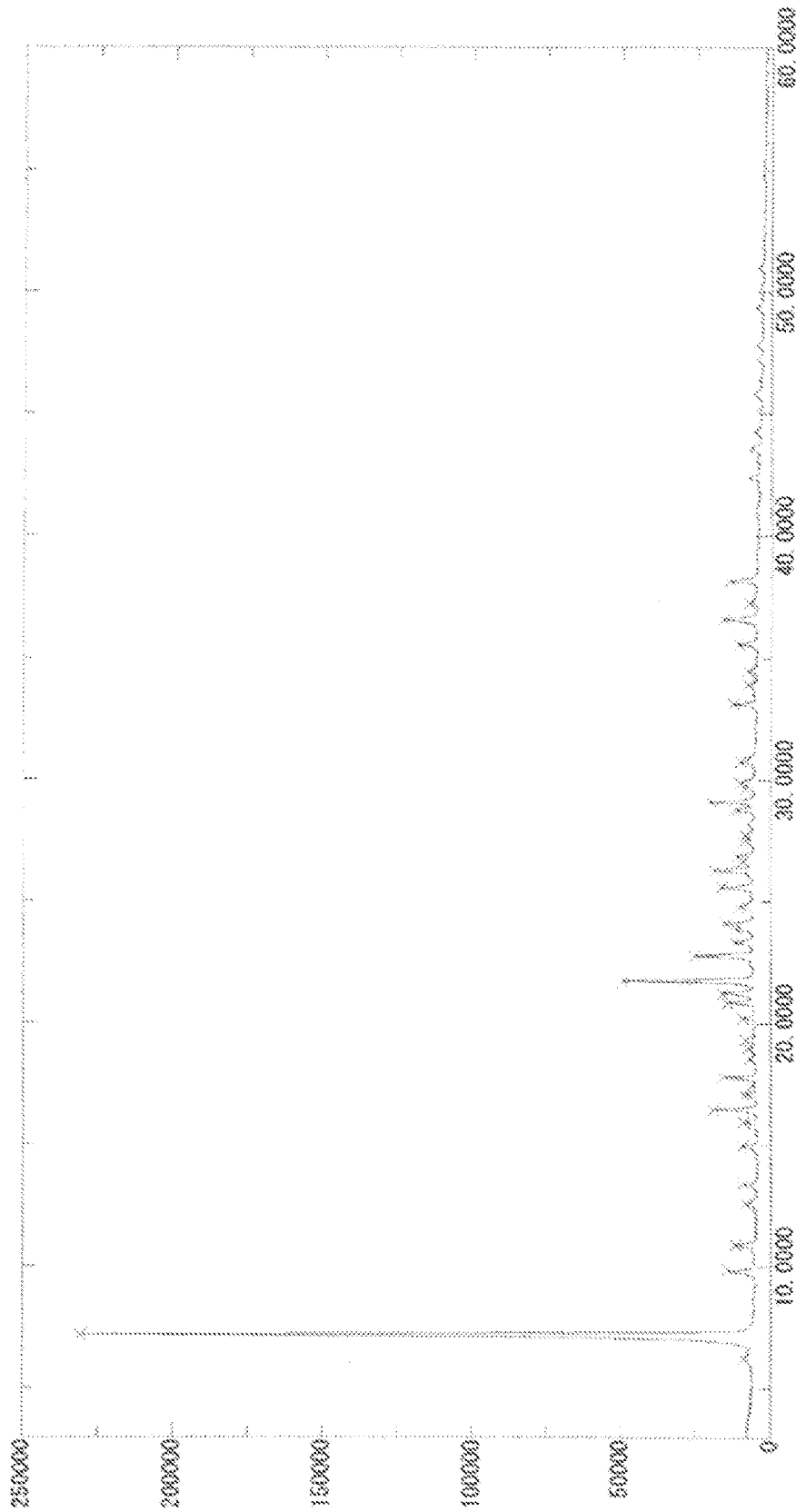
FIG. 1 illustrates the results of powder X-ray diffraction of a crystal of 3SL sodium salt n-hydrate obtained in Example 1. The vertical axis represents an intensity (cps), and the horizontal axis represents a diffraction angle (2θ°).

The crystal of the present invention is a crystal of 3SL sodium salt n-hydrate (wherein n is any number of 0 to 9, and when n is 0, it is referred to as 3SL sodium salt anhydrate).

Whether the crystal of the present invention is a crystal of 3SL can be confirmed by, for example, analysis using HPLC. As analysing conditions in the analysis using HPLC, for example, the following conditions can be mentioned.

Column: DionexCarboPac (trademark) PA1 BioLC (trademark), 4×250 mm
Guard column: DionexCarboPac (trademark) PA1 BioLC (trademark), 4×50 mm
Column temperature: 30° C.
Flow rate: 1 mL/min
Eluent: 0.5 M sodium hydroxide/0.3 M sodium acetate aqueous solution Whether the crystal is a crystal of 3SL can also be confirmed by analysis using a powder X-ray diffraction apparatus. Analysis by powder X-ray diffraction can be performed, for example, using a powder X-ray diffraction apparatus (XRD), Ultima IV (manufactured by Rigaku Corporation), using CuKα being used as an X-ray source, according to the attached instruction book.

Whether the crystal of 3SL is a crystal of a sodium salt can be confirmed by measuring a content of sodium contained in the crystal. The content of sodium can be measured, for example, using an atomic absorption spectrophotometer Z-2310 (manufactured by Hitachi High-Technologies Corporation) according to the attached instruction book.

For example, whether the crystal of the present invention is a crystal of monosodium salt can be confirmed by the fact that the content of sodium in the crystal is generally 3.5±1.5 wt %, preferably 3.5±1.0 wt %, and most preferably 3.5±0.5 wt %, in terms of an anhydrate.

As the crystal of the present invention, a crystal of 3SL sodium salt n-hydrate in which a value of n in the n hydrate is from 4 to 9, preferably from 5.0 to 8.0, more preferably 8.0 or 5.0, and most preferably 8.0 can be mentioned.

Whether the value of n in the n hydrate is from 4 to 9 can be confirmed by the fact that a water content in the crystal is generally from 9.0 to 20.0 wt %. Whether the value of n is from 5.0 to 8.0 can be confirmed by the fact that a water content measured in a similar manner is generally from 12.0 to 18.0 wt %.

The water content in the crystal can be measured by, for example, the Karl-Fisher method. The water content measurement by the Karl-Fisher method can be carried out, for example, by a heating vaporization method (110° C. to 171° C., 14 minutes) using an automatic water content measuring device AQV-2200 (manufactured by Hiranuma Sangyo Co., Ltd.) according to the instruction book.

Whether the value of n is 8.0 can be confirmed by the fact that a water content measured in a similar manner is generally 18.0±1.5 wt %. In addition, whether the value of n is 5.0 can be confirmed by the fact that a water content measured in a similar manner is generally 12.1±1.5 wt %.

The crystal of the present invention in which the value of n in the n hydrate is from 4 to 9 is preferably a crystal of 3SL sodium salt n-hydrate which has peaks at diffraction angles (2θ°) described in the following (i) in powder X-ray diffraction using CuKα as the X-ray source, more preferably a crystal of 3SL sodium salt n-hydrate which further has peaks at diffraction angles (2θ°) described in the following (ii) in addition to the diffraction angles (2θ°) described in the following (i), and further more preferably a crystal of 3SL sodium salt n-hydrate which further has peaks at diffraction angles (2θ°) described in the following (iii) in addition to the diffraction angles (2θ°) described in the following (i) and (ii).

(i) 7.2±0.2°, preferably 7.2±0.1°, 10.9±0.2°, preferably 10.9±0.1°, 22.7±0.2°, preferably 22.7±0.1°, 21.2±0.2°, preferably 21.2±0.1°, and 9.8±0.2°, preferably 9.8±0.1°

(ii) 23.3±0.2°, preferably 23.3±0.1°, 21.8±0.2°, preferably 21.8±0.1°, 17.1±0.2°, preferably 17.1±0.1°, 17.8±0.2°, preferably 17.8±0.1°, and 24.1±0.2°, preferably 24.1±0.1°

(iii) 24.7±0.2°, preferably 24.7±0.1°, 16.4±0.2°, preferably 16.4±0.1°, 25.6±0.2°, preferably 25.6±0.1°, 20.9±0.2°, preferably 20.9±0.1°, and 23.9±0.2°, preferably 23.9±0.1°

Figure 2:
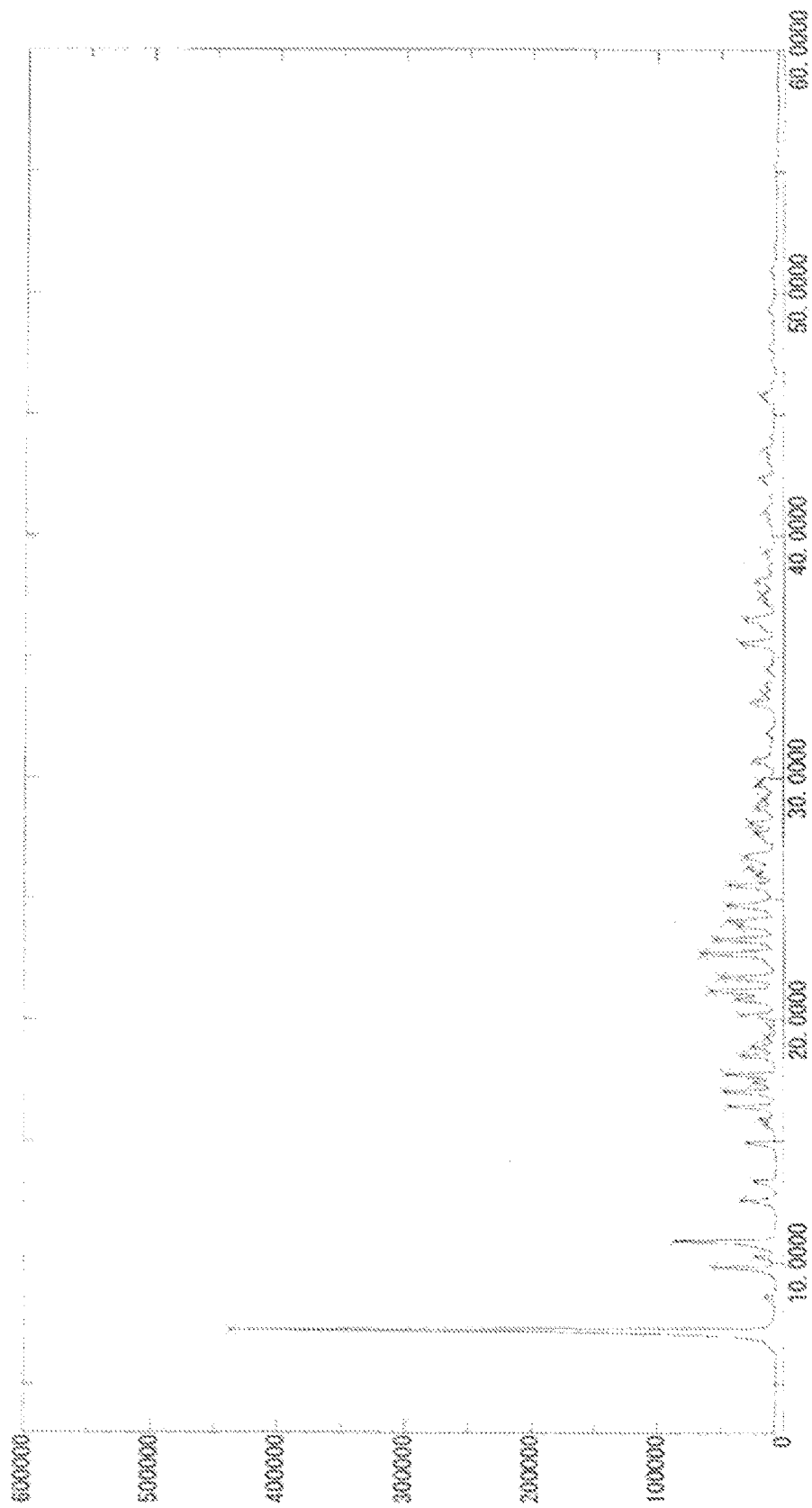
FIG. 2 illustrates the results of powder X-ray diffraction of a crystal of 3SL sodium salt 8.0-hydrate obtained in Example 2. The vertical axis represents an intensity (cps), and the horizontal axis represents a diffraction angle (2θ°).
Figure 5:
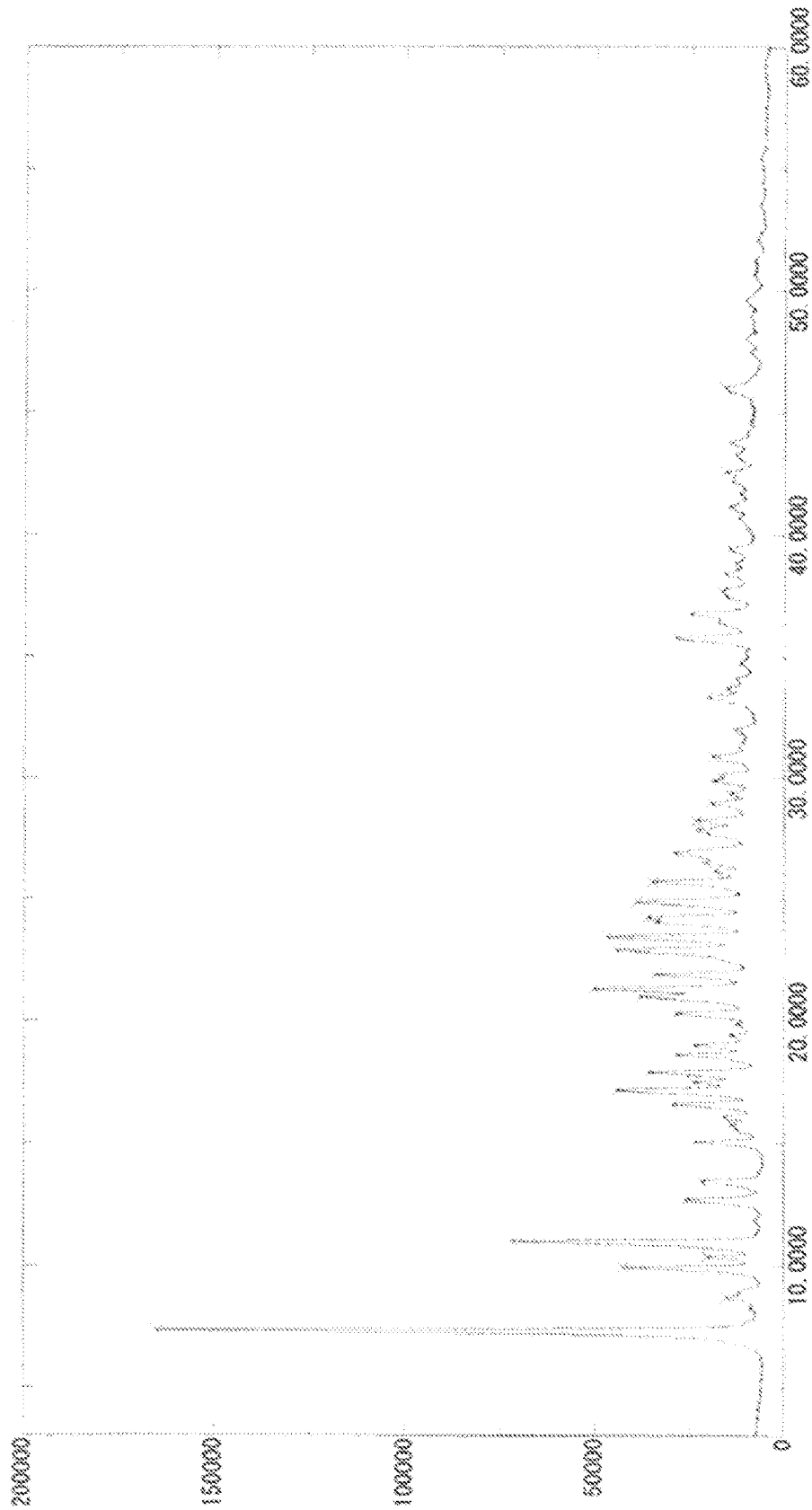
FIG. 5 illustrates the results of powder X-ray diffraction of a crystal of 3SL sodium salt 5.0-hydrate obtained in Example 5. The vertical axis represents an intensity (cps), and the horizontal axis represents a diffraction angle (2θ°).

More specific examples of the crystal of the present invention in which the value of n in the n hydrate is from 4 to 9 may include a crystal of 3SL sodium salt n-hydrate whose powder X-ray diffraction pattern using CuKα as the X-ray source is defined by the pattern shown in FIG. 1 and the values of diffraction angle shown in Table 1, a crystal of 3SL sodium salt 8.0-hydrate whose powder X-ray diffraction pattern is defined by the pattern shown in FIG. 2 and the values of diffraction angle shown in Table 2, and a crystal of 3SL sodium salt 5.0-hydrate whose powder X-ray diffraction pattern is defined by the pattern shown in FIG. 5.

Figure 3:
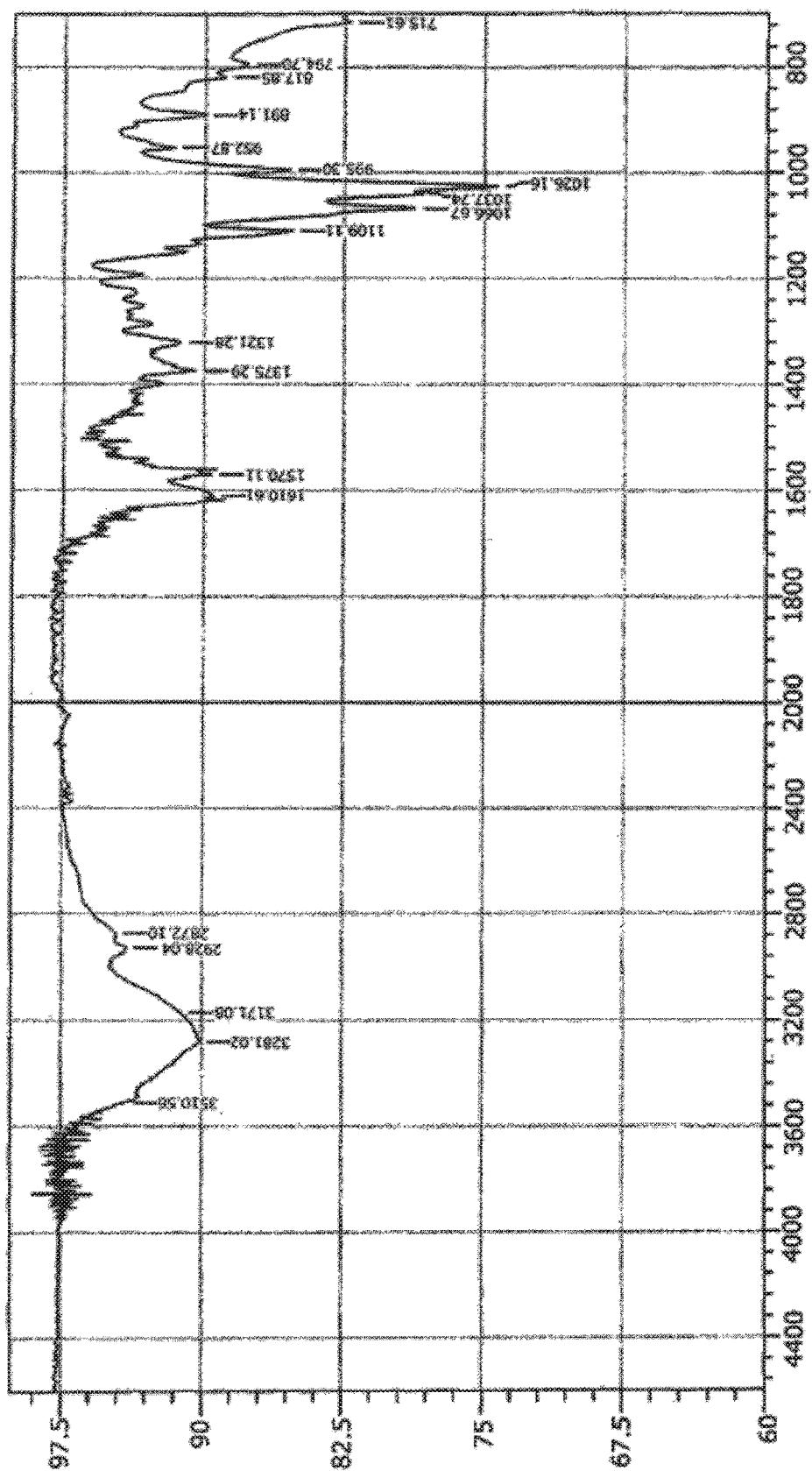
FIG. 3 illustrates the results of infrared spectroscopic (IR) analysis of the crystal of 3SL sodium salt 8.0-hydrate obtained in Example 2. The vertical axis represents light transmittance (% T), and the horizontal axis represents wave number (1/cm).

Further, examples thereof may include a crystal of 3SL sodium salt 8.0-hydrate which shows the infrared absorption spectrum illustrated in FIG. 3 when subjected to the infrared spectroscopic (IR) analysis.

Infrared spectroscopic (IR) analysis can be carried out, for example, using Model FTIR-8400 (manufactured by Shimadzu Corporation) according to the attached instruction book. Further, examples thereof may include a crystal of 3SL sodium salt 8.0-hydrate which is defined by the values shown in Table 7 in single crystal X-ray structure analysis.

Single crystal X-ray structure analysis can be carried out, for example, using R-AXIS RAPD-F (manufactured by Rigaku Corporation) according to the instruction book. Specifically, for example, a single crystal of 3SL sodium salt is placed on a diffractometer, and a diffraction image is measured using an X-ray with a predetermined wavelength in the air at room temperature or in an inert gas stream at a predetermined temperature. From a set of a Miller index calculated from the diffraction image and a diffraction intensity, structure determination by a direct method and structure refinement by a least-squares method are performed, whereby a single crystal structure is obtained.

In one embodiment, a crystalline form of 3SL sodium salt 8.0-hydrate preferably shows single crystal X-ray crystallographic analysis results with roughly the following crystal parameters, that is: a unit cell size: a=11.2942 Å; b=13.3269 Å; c=24.4525 Å; V=3680.5 Å$^3$; Z=4; a calculated density ($D_{calc}$, gcm$^{-3}$) of 1.443 gcm$^{-3}$; and a space group of P2$_1$2$_1$2$_1$, when measured at approximately −173° C. in single crystal X-ray structure analysis.

In addition, in one embodiment, a crystalline form of 3SL sodium salt 8.0-hydrate is preferably represented by a formula Na$^+$(C$_{23}$H$_{38}$NO$_{19}$)$^-$·8H$_2$O.

A crystal of 3SL sodium salt n-hydrate, in which a value of n in the n hydrate is equal to or greater than 0 and less than 4, preferably from 1 to 3.5, and more preferably 2.0, 3.5, or 1.4, is also the crystal of the present invention.

The crystal in which the value of n of the n-hydrate is equal to or greater than 0 and less than 4 can be confirmed by, for example, the fact that the water content as measured using the Karl-Fisher method is generally from 0 to 10.0 wt %. The crystal in which the value of n of the n-hydrate is from 1 to 3.5 can be confirmed by the fact that the water content as measured in a similar manner is generally from 2.0 to 9.0 wt %. The water content measurement by the Karl-Fisher method can be carried out by the same method as described above.

Whether the value of n is 2.0 can be confirmed by the fact that the water content as measured in a similar manner is generally 5.2±1.5 wt %. In addition, whether the value of n is 3.5 can be confirmed by the fact that the water content as measured in a similar manner is generally 8.8±1.5 wt %. In addition, whether the value of n is 1.4 can be confirmed by the fact that the water content as measured in a similar manner is generally 3.7±1.5 wt %.

The crystal of the present invention in which the value of n in the n hydrate is equal to or greater than 0 and less than 4 is preferably a crystal of 3SL sodium salt n-hydrate which has peaks at diffraction angles (2θ°) described in the following (iv) in powder X-ray diffraction using CuKα as the X-ray source, more preferably a crystal of 3SL sodium salt n-hydrate which further has peaks at diffraction angles (2θ°) described in the following (v) in addition to the diffraction angles (2θ°) described in the following (iv), and furthermore preferably a crystal of 3SL sodium salt n-hydrate which further has peaks at diffraction angles (2θ°) described in the following (vi) in addition to the diffraction angles (2θ°) described in the following (iv) and (v).

(iv) 8.9±0.2°, preferably 8.9±0.1°, 17.1±0.2°, preferably 17.1±0.1°, 15.5±0.2°, preferably 15.5±0.1°, 19.3±0.2°, preferably 19.3±0.1°, and 20.9±0.2°, preferably 20.9±0.1°

(v) 27.4±0.2°, preferably 27.4±0.1°, 13.3±0.2°, preferably 13.3±0.1°, 22.5±0.2°, preferably 22.5±0.1°, 11.8±0.2°, preferably 11.8±0.1°, and 23.7±0.2°, preferably 23.7±0.1°

(vi) 25.0±0.2°, preferably 25.0±0.1°, 10.8±0.2°, preferably 10.8±0.1°, 17.9±0.2°, preferably 17.9±0.1°, 20.0±0.2°, preferably 20.0±0.1°, and 21.8±0.2°, preferably 21.8±0.1°

Figure 4:
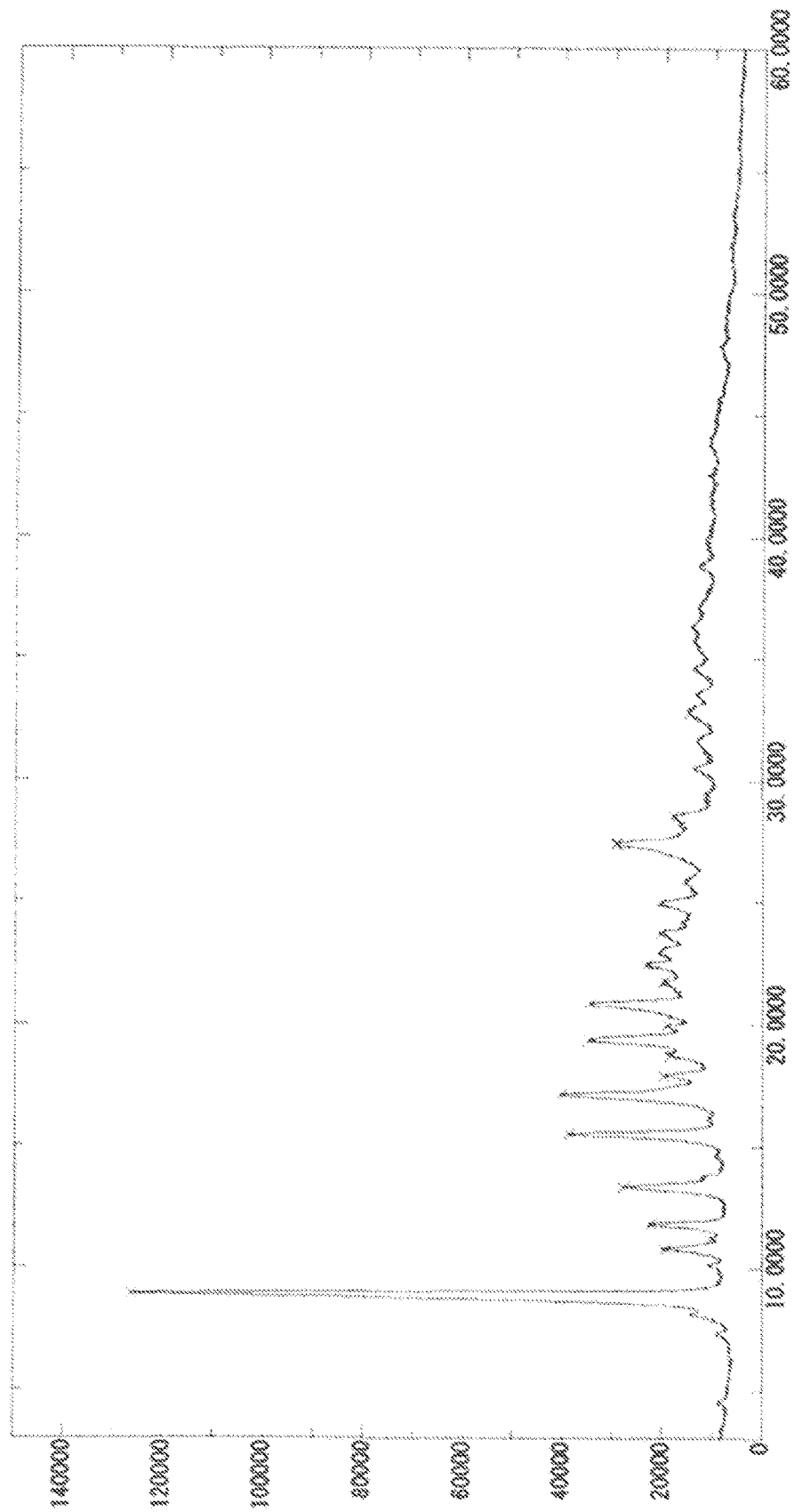
FIG. 4 illustrates the results of powder X-ray diffraction of a crystal of 3SL sodium salt 2.0-hydrate obtained in Example 3. The vertical axis represents an intensity (cps), and the horizontal axis represents a diffraction angle (2θ°).
Figure 6:
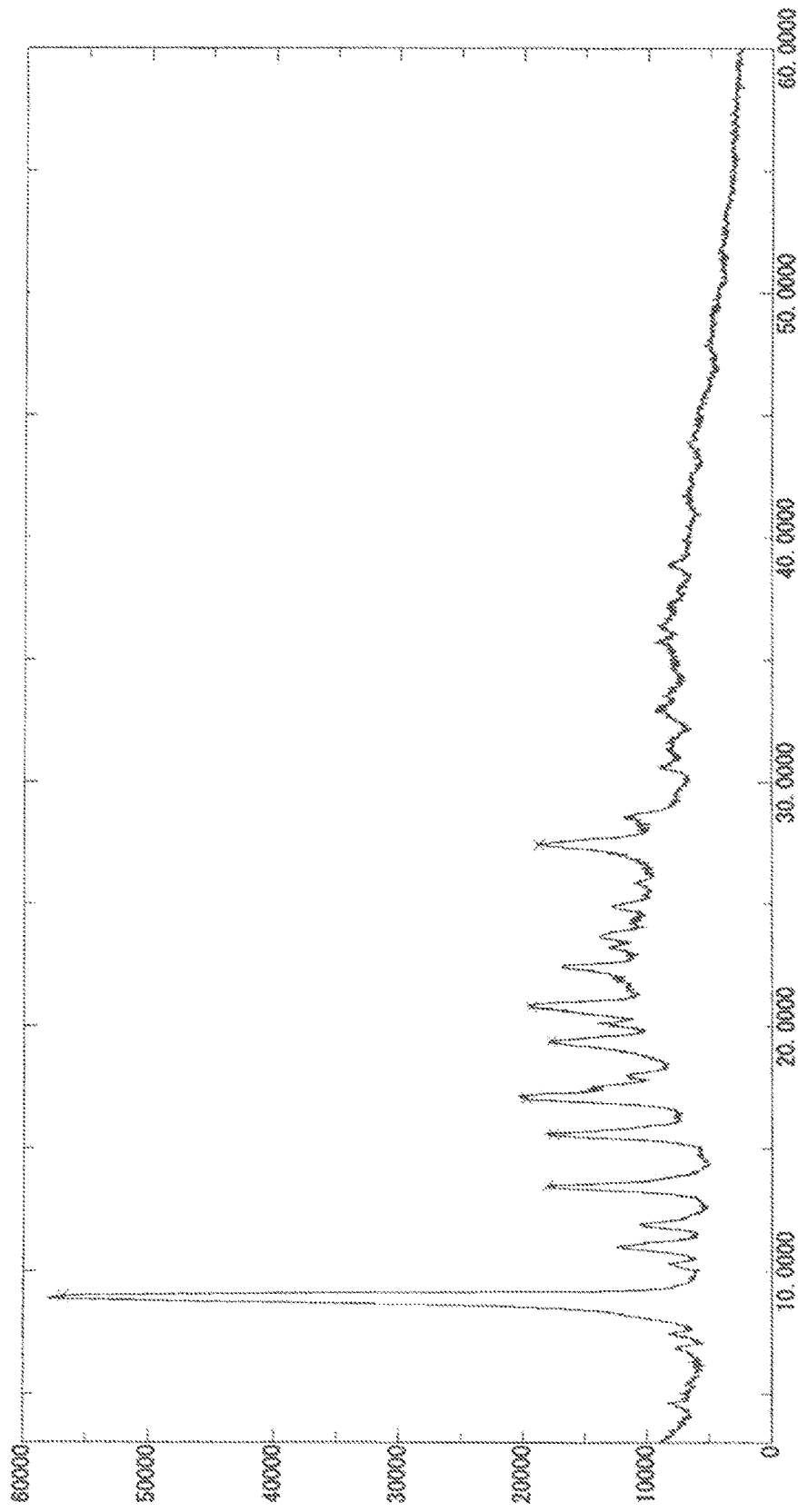
FIG. 6 illustrates the results of powder X-ray diffraction of a crystal of 3SL sodium salt 1.4-hydrate obtained in Example 7. The vertical axis represents an intensity (cps), and the horizontal axis represents a diffraction angle (2θ°).

More specific examples of the crystal of the present invention in which the value of n in the n hydrate is equal to or greater than 0 and less than 4 may include a crystal of 3SL sodium salt 2.0-hydrate whose powder X-ray diffraction pattern using CuKα as the X-ray source is defined by the pattern shown in FIG. 4 and the values of diffraction angle shown in Table 6, and a crystal of 3SL sodium salt 1.4-hydrate whose powder X-ray diffraction pattern is defined by the pattern shown in FIG. 6.

2. Process for Producing Crystal of the Present Invention

The process for producing the crystal of the present invention is each production process described in the following 2-1 to 2-3.

2-1. Process for Producing Crystal of the Present Invention 1

As a process for producing the crystal of the present invention in which the value of n of the n hydrate of the above 1 is from 4 to 9, a process for producing a crystal of 3SL sodium salt n-hydrate (wherein n is any number of 4 to 9) which includes a step of precipitating a crystal of 3SL sodium salt n-hydrate (wherein n is any number of 4 to 9) by causing a 3SL aqueous solution containing a sodium-containing compound to be left to stand or to be stirred, and a step of collecting the crystal of 3SL sodium salt n-hydrate (wherein n is any number of 4 to 9) from the aqueous solution may be mentioned.

The value of n in the n hydrate is preferably from 5.0 to 8.0, and most preferably 8.0. 3SL contained in the 3SL sodium salt aqueous solution may be produced by any of production methods such as a fermentation method, an enzymatic method, an extraction method from a natural product, and a chemical synthesis method.

In a case where a solid material that obstructs crystallization is contained in the 3SL aqueous solution, the solid material can be removed using centrifugal separation, filtration, a ceramic filter, or the like.

In addition, in a case where a water-soluble impurity or salt that obstructs crystallization is contained in the 3SL aqueous solution, the water-soluble impurity or salt can be removed by passing the aqueous solution through a column packed with an ion exchange resin, or the like.

In addition, in a case where a hydrophobic impurity that obstructs crystallization is contained in the 3SL aqueous solution, the hydrophobic impurity can be removed by passing the aqueous solution through a column packed with a synthetic adsorption resin, active carbon, or the like.

The aqueous solution can be adjusted such that the concentration of 3SL is generally 450 g/kg or more, preferably 500 g/kg or more, more preferably 550 g/kg or more, and most preferably 600 g/kg or more. In order to adjust the concentration in the aqueous solution to the above concentration, the aqueous solution can be concentrated by a general concentration method such as a heating concentration method or a reduced-pressure concentration method.

The sodium-containing compound may include, for example, a basic compound such as sodium hydroxide, or a neutral salt such as carbonate of sodium, sulfate of sodium, nitrate of sodium, or chloride of sodium. As the neutral salt, specifically, sodium carbonate, sodium sulfate, sodium nitrate, or sodium chloride may be mentioned.

In a case where a basic compound is used as the sodium-containing compound, the 3SL aqueous solution containing a sodium-containing compound and having a pH of generally from 3.0 to 9.0, preferably from 4.5 to 8.5, and most preferably from 5.5 to 8.0, can be obtained by adjusting the pH of the 3SL aqueous solution using the basic compound.

By causing the aqueous solution to be left to stand or to be stirred, a crystal of 3SL sodium salt n-hydrate (wherein n is any number of 4 to 9) can be precipitated. The temperature at which the solution is left to stand or stirred may be generally from 0° C. to 40° C., preferably from 5° C. to 35° C., and most preferably from 10° C. to 30° C. The time for which the solution is left to stand or stirred may be generally from 2 to 72 hours, preferably from 3 to 60 hours, and most preferably from 5 to 48 hours.

After the crystal of 3SL sodium salt n-hydrate (wherein n is any number of 4 to 9) is precipitated as described above, the precipitated crystal may be further grown by aging generally for 1 to 48 hours, preferably for 1 to 24 hours, and most preferably for 1 to 12 hours.

The precipitated crystal being grown by aging means stopping the step of precipitating the crystal of 3SL sodium salt n-hydrate (wherein n is any number of 4 to 9) so that the crystal is grown. After the crystal is grown by aging, the step of precipitating the crystal of 3SL sodium salt n-hydrate (wherein n is any number of 4 to 9) may be resumed.

The crystal being grown means increasing the crystal based on the precipitated crystal. Growing by aging of the crystal is carried out mainly for the purpose of growing the crystal. However, simultaneously with the growth of the crystal, precipitation of new crystals may occur.

The method for collecting the crystal of 3SL sodium salt n-hydrate (wherein n is any number of 4 to 9) is not particularly limited and may include, for example, collection by filtration, pressure filtration, suction filtration, centrifugal separation, and the like. Furthermore, in order to reduce the adhesion of the mother liquid to the crystal and thereby improve the quality of the crystal, the crystal may be appropriately washed after collecting the crystal.

The solution used for crystal washing is not particularly limited, and water, methanol, ethanol, acetone, n-propanol, isopropyl alcohol, and a solution prepared by mixing one kind or a plurality of kinds of members selected from these at a predetermined ratio may be used.

The thus obtained wet crystal is dried, whereby the crystal of the present invention can be obtained. As for the drying conditions, any method may be used as long as the form of the crystal of 3SL sodium salt n-hydrate (wherein n is any number of 4 to 9) can be retained, and for example, reduced-pressure drying, vacuum drying, fluidized bed drying, forced air drying, and the like may be mentioned.

The drying temperature may be any temperature as long as the form of the crystal can be retained and the adhered water or solvent can be removed, and the temperature may be preferably 40° C. or less, more preferably 35° C. or less, and most preferably 30° C. or less. The time required for drying may be any time to the extent that the form of the crystal can be retained and the adhered water or solvent can be removed, and the time may be preferably from 1 to 60 hours and more preferably from 1 to 48 hours.

According to the above-mentioned crystallization conditions, a high-purity crystal of 3SL sodium salt n-hydrate (wherein n is any number of 4 to 9) can be obtained. The purity of the crystal of 3SL sodium salt n-hydrate (wherein n is any number of 4 to 9) may be generally 94% or more, preferably 95% or more, more preferably 96% or more, and most preferably 97% or more. The purity of the crystal can be confirmed by, for example, the analysis using HPLC described in the above 1.

Examples of the crystal of 3SL sodium salt n-hydrate (wherein n is any number of 4 to 9) which can be produced by the above-mentioned production process may include a crystal of 3SL sodium salt n-hydrate whose powder X-ray diffraction pattern using CuKα as the X-ray source is defined by the pattern shown in FIG. 1 and the values of diffraction angle shown in Table 1.

The obtained crystal of 3SL sodium salt n-hydrate (wherein n is any number of 4 to 9) is left to stand for 1 to 20 hours under a condition of 50° C. or less and dried, so that a crystal of n-hydrate (wherein n is any number of 4 to 9) having a smaller n than the n-hydrate (wherein n is any number of 4 to 9).

2-2. Process for Producing Crystal of the Present Invention 2

As a process for producing the crystal of the present invention in which the value of n of the n hydrate of the above 1 is from 4 to 9, a process for producing a crystal of 3SL sodium salt n-hydrate (wherein n is any number of 4 to 9) which includes a step of adding a crystal of 3SL sodium salt n-hydrate (wherein n is any number of 4 to 9) as a seed crystal to a 3SL aqueous solution containing a sodium-containing compound, a step of causing a crystal of 3SL sodium salt n-hydrate (wherein n is any number of 4 to 9) to be precipitated in the aqueous solution, and a step of collecting the crystal of 3SL sodium salt n-hydrate (wherein n is any number of 4 to 9) from the aqueous solution may be mentioned.

The value of n in the n hydrate is preferably from 5.0 to 8.0, and most preferably 8.0. As 3SL contained in the aqueous solution of 3SL sodium salt, the same as described in the above 2-1 can be used.

In a case where a solid material that obstructs crystallization, a water-soluble impurity or salt that obstructs crystallization, or a hydrophobic impurity that obstructs crystallization is contained in the 3SL aqueous solution, the same process as in the above 2-1 can be adopted.

The aqueous solution can be adjusted such that the concentration of 3SL is generally 400 g/L or more, preferably 500 g/L or more, more preferably 600 g/L or more, and most preferably 700 g/L or more. In order to adjust the concentration in the aqueous solution to the concentration above, the aqueous solution can be concentrated by a general concentration method such as a heating concentration method or a reduced-pressure concentration method.

Regarding the sodium-containing compound, the same as in the above 2-1 is applied. In a case where a basic compound is used as the sodium-containing compound, the 3SL aqueous solution containing a sodium-containing compound and having a pH of generally from 3.0 to 9.0, preferably from 4.5 to 8.5, and most preferably from 5.5 to 8.0, can be obtained by adjusting the pH of the 3SL aqueous solution using the basic compound.

In the process for producing the crystal of the present invention of 2-2, 3SL sodium salt n-hydrate (wherein n is any number of 4 to 9) is added as a seed crystal to a 3SL aqueous solution containing a sodium-containing compound.

As the seed crystal, for example, the crystal of 3SL sodium salt n-hydrate (wherein n is any number of 4 to 9) obtained by the process of the above 2-1 can be used. The seed crystal is added so that the concentration in the aqueous solution is generally from 0.2 to 15 wt %, preferably from 0.4 to 10 wt %, and most preferably from 0.7 to 7 wt %.

The method for precipitating the crystal of 3SL sodium salt n-hydrate (wherein n is any number of 4 to 9) in the aqueous solution may include, for example, a method in which the aqueous solution is cooled, a method in which the aqueous solution is concentrated at a reduced pressure, a method in which an alcohol solution is added or added dropwise in the aqueous solution, and the like. In addition, one or more methods of these methods may be combined and used.

In the method in which the aqueous solution is cooled, the temperature of the aqueous solution may be generally from 0° C. to 40° C., preferably from 0° C. to 35° C., and most preferably from 0° C. to 30° C. In the method in which the aqueous solution is cooled, the time required for cooling may be generally from 2 to 100 hours, preferably from 3 to 70 hours, and most preferably from 5 to 50 hours.

In the method in which the aqueous solution is concentrated at a reduced pressure, the temperature of the aqueous solution may be generally from 0° C. to 100° C., preferably from 10° C. to 90° C., and most preferably from 20° C. to 80° C. In the method in which the aqueous solution is concentrated at a reduced pressure, the time required for the reduced pressure may be generally from 2 to 100 hours, preferably from 3 to 70 hours, and most preferably from 5 to 50 hours.

In the method in which an alcohol solution is added or added dropwise in the aqueous solution whereby the crystal of 3SL sodium salt n-hydrate (wherein n is any number of 4 to 9) is precipitated, a seed crystal is added immediately before the addition or dropwise addition of the alcohol solution is started, or after the alcohol solution is added or added dropwise and before the crystal of 3SL sodium salt n-hydrate (wherein n is any number of 4 to 9) is precipitated.

The seed crystal may be added generally within 0 to 5 hours, preferably within 0 to 4 hours, and most preferably within 0 to 3 hours after the addition or dropwise addition of the alcohol solution is started.

The alcohol solution may be a mixture of a plurality of kinds of alcohols, or a mixture of an alcohol and another organic solvent or water so far as it can be used in the process of the present invention, and may be preferably a C1 to C6 alcohol, more preferably a C1 to C3 alcohol, further more preferably an alcohol selected from the group consisting of methanol, ethanol, n-propanol, and isopropyl alcohol, still further more preferably methanol or ethanol, and most preferably ethanol.

In addition, in a case where the alcohol solution used in the present invention is an alcohol aqueous solution, the water content may be generally 40 wt % or less, preferably 20 wt % or less, more preferably 10 wt % or less, and most preferably 5 wt % or less.

The temperature of the aqueous solution when the alcohol solution is added or added dropwise may be any temperature as long as 3SL is not decomposed, and the temperature may be generally 45° C. or less, preferably 40° C. or less, more preferably 35° C. or less, and most preferably 30° C. or less. A lower limit value of the temperature may be generally 0° C. or more, and preferably 10° C. or more.

The amount of the alcohol solution to be added or added dropwise is generally from 0.1 to 30 times, preferably from 0.2 to 25 times, most preferably from 0.3 to 10 times the amount of the aqueous solution. The time required for adding or adding dropwise the alcohol solution to the aqueous solution may be generally from 1 to 48 hours, preferably from 2 to 30 hours, and most preferably from 3 to 20 hours.

After the crystal of 3SL sodium salt n-hydrate (wherein n is any number of 4 to 9) is precipitated as described above, the precipitated crystal may be further grown by aging generally for 1 to 48 hours, preferably for 1 to 24 hours, and most preferably for 1 to 12 hours.

The precipitated crystal being grown by aging means stopping the step of precipitating the crystal of 3SL sodium salt n-hydrate (wherein n is any number of 4 to 9) so that the crystal is grown. After the crystal is grown by aging, the step of precipitating the crystal of 3SL sodium salt n-hydrate (wherein n is any number of 4 to 9) may be resumed.

Regarding the growth of the crystal, the same as the above 2-1 is applied.

After the crystal of 3SL sodium salt n-hydrate (wherein n is any number of 4 to 9) is precipitated by the above-mentioned method, the crystal of 3SL sodium salt n-hydrate (wherein n is any number of 4 to 9) may be collected by the same step as in the above 2-1 method.

By the above-mentioned method, a high-purity crystal of 3SL sodium salt n-hydrate (wherein n is any number of 4 to 9) can be obtained. The purity of the crystal of 3SL sodium salt n-hydrate (wherein n is any number of 4 to 9) may be generally 94% or more, preferably 95% or more, more preferably 96% or more, and most preferably 97% or more. The purity of the crystal can be confirmed by, for example, the analysis using HPLC described in the above 1.

Examples of the crystal of 3SL sodium salt n-hydrate (wherein n is any number of 4 to 9) which can be produced by the above-mentioned production process may include a crystal of 3SL sodium salt 8.0-hydrate whose powder X-ray diffraction pattern using CuKα as the X-ray source is defined by the pattern shown in FIG. 2 and the values of diffraction angle shown in Table 2.

Further, examples thereof may include a crystal of 3SL sodium salt 8.0-hydrate which shows the infrared absorption spectrum illustrated in FIG. 3 when subjected to the infrared spectroscopic (IR) analysis. Further, examples thereof may include a crystal of 3SL sodium salt 8.0-hydrate which is defined by the values shown in Table 7 in single crystal X-ray structure analysis.

The obtained crystal of 3SL sodium salt n-hydrate (wherein n is any number of 4 to 9) is left to stand for 1 to 20 hours under a condition of 50° C. or less and dried, so that a crystal of n-hydrate (wherein n is any number of 4 to 9) having a smaller n than the n-hydrate (wherein n is any number of 4 to 9) can be obtained.

Examples of such a crystal of 3SL sodium salt n-hydrate (wherein n is any number of 4 to 9) may include a crystal of 3SL sodium salt 5.0-hydrate whose powder X-ray diffraction pattern using CuKα as the X-ray source is defined by the pattern shown in FIG. 5.

2-3. Process for Producing Crystal of the Present Invention 3

As a process for producing the crystal of the present invention in which the value of n of the n hydrate of the above 1 is equal to or greater than 0 and less than 4, a process for producing a crystal of 3SL sodium salt n-hydrate (wherein n is any number which is equal to or greater than 0 and less than 4) which includes a step of performing forced air drying of the crystal of 3SL sodium salt n-hydrate (wherein n is any number of 4 to 9) obtained in the above 2-1 or 2-2 at 45° C. or more for 20 hours or more, or a step of performing vacuum drying of the same at 25° C. or more for 48 hours or more may be mentioned. The value of n in the n-hydrate in the obtained crystal of 3SL sodium salt n-hydrate may be preferably from 1 to 3.5.

As a drying method, for example, forced air drying or vacuum drying may be used. The drying temperature in a case where the crystal is dried with forced air may be preferably 45° C. or more, and more preferably 50° C. or more. The time required for the forced air drying may be preferably 20 hours or more. The drying temperature in a case where the crystal is vacuum-dried may be preferably 25° C. or more, and more preferably 30° C. or more. The time required for the vacuum drying may be preferably 48 hours or more.

By the above-mentioned method, a high-purity crystal of 3SL sodium salt n-hydrate (wherein n is any number which is equal to or greater than 0 and less than 4) can be obtained. The purity of the crystal of 3SL sodium salt n-hydrate (wherein n is any number which is equal to or greater than 0 and less than 4) may be generally 93% or more, preferably 94% or more, more preferably 95% or more, and most preferably 96% or more. The purity of the crystal can be confirmed by, for example, the analysis using HPLC described in the above 1.

Examples of the crystal of 3SL sodium salt n-hydrate (wherein n is any number which is equal to or greater than 0 and less than 4) which can be produced by the above-mentioned production process may include a crystal of 3SL sodium salt 2.0-hydrate whose powder X-ray diffraction pattern using CuKα as the X-ray source is defined by the pattern shown in FIG. 4 and the values of diffraction angle shown in Table 6, and a crystal of 3SL sodium salt 1.4-hydrate whose powder X-ray diffraction pattern is defined by the pattern shown in FIG. 6.

Reference Example 1

Obtaining of Noncrystalline Amorphous 3SL Sodium Salt

A sodium hydroxide aqueous solution was added to an aqueous solution containing 100 g of 3SL in terms of free form so that the pH was adjusted 6.40 and the volume was made up to 0.5 L. A part of this aqueous solution was freeze-dried, whereby a white powder was obtained. The powder X-ray diffraction of the powder was measured, and as a result, an X-ray diffraction peak was not confirmed. Therefore, the powder was found to be noncrystalline amorphous.

Reference Example 2

Study of Obtaining Crystal of 3SL Sodium Salt by Concentration 30 mL of an aqueous solution (pH 6.81) of 3SL sodium salt at 169 g/L in terms of sodium salt was concentrated (50° C., 20 hPa, 30 minutes) to obtain 6.3 g of a white solid material. As a result of observation using a polarized light microscope, it was confirmed that the solid material was an indefinite-shaped candy-like solid material and was noncrystalline amorphous. From the above, it was found that a crystal of 3SL sodium salt was not obtained by this method.

Reference Example 3

Study of Obtaining Crystal of 3SL Sodium Salt by Mixing with Organic Solvent (1)

Obtaining a crystal of 3SL sodium salt was tried with reference to Patent Document 2. 10 mL of 95%-methanol was added to 6.3 g of noncrystalline amorphous 3SL sodium salt obtained by the method of Reference Example 1 and stirred for 24 hours to obtain a white transparent solution in which the amorphous 3SL sodium salt was dissolved. Further, 30 mL of 100%-methanol was added to the solution to precipitate a white precipitate.

As a result of observation using a polarized light microscope, it was confirmed that the obtained precipitate was an indefinite-shaped candy-like solid and was noncrystalline amorphous. From the above, it was found that a crystal of 3SL sodium salt was not obtained by this method.

Reference Example 4

Study of Obtaining Crystal of 3SL Sodium Salt by Mixing with Organic Solvent (2)

Obtaining a crystal of 3SL sodium salt was tried with reference to Patent Document 2. 10 mL of 95%-ethanol was added to 6.3 g of noncrystalline amorphous 3SL sodium salt obtained by the method of Reference Example 1 and stirred for 24 hours to obtain a white precipitate.

As a result of observation using a polarized light microscope, it was confirmed that the obtained precipitate was an indefinite-shaped candy-like solid showing no polarized light and was noncrystalline amorphous. From the above, it was found that a crystal of 3SL sodium salt was not obtained by this method.

Reference Example 5

Study of Obtaining Crystal of 3SL Sodium Salt by Mixing with Organic Solvent (3)

Obtaining a crystal of 3SL sodium salt was tried with reference to Patent Document 2. 10 mL of 95%-isopropyl alcohol was added to 6.5 g of noncrystalline amorphous 3SL sodium salt obtained by the method of Reference Example 1 and stirred for 24 hours to obtain a white precipitate.

As a result of observation using a polarized light microscope, it was confirmed that the obtained precipitate was an indefinite-shaped candy-like solid showing no polarized light and was noncrystalline amorphous. From the above, it was found that a crystal of 3SL sodium salt was not obtained by this method.

EXAMPLES

Examples are described below, but the present invention is not limited to the following Examples. In addition, "%" in tables of the following Examples means "wt/o" unless otherwise specified.

Example 1

Obtaining Crystal of 3SL Sodium Salt n-Hydrate

To 50.3 mg of a 3SL sodium reagent (amorphous salt, manufactured by Carbosynth Limited), 25 μL of water was added, and dissolution was carried out while heating to 50° C. The aqueous solution was stirred at room temperature for 12 hours, whereby a crystal was naturally crystallized. The aqueous solution was naturally dried at room temperature for 48 hours to obtain 60 mg of a crystal of 3SL sodium salt n-hydrate.

From the powder X-ray diffraction results of the obtained crystal, diffraction angles of the peaks in which the relative intensity ratio ($I/I_0$) was 4 or more are shown in Table 1. In the table, "2θ" indicates the diffraction angle (2θ°), and "Relative Intensity" indicates the relative intensity ratio ($I/I_0$).

TABLE 1

| 2θ | Relative Intensity |
|---|---|
| 6.3 | 4 |
| 7.2 | 100 |
| 9.8 | 7 |
| 10.9 | 6 |
| 12.6 | 4 |
| 13.4 | 5 |
| 14.9 | 5 |
| 15.9 | 4 |
| 16.4 | 9 |
| 17.1 | 4 |
| 17.4 | 3 |
| 17.7 | 7 |
| 18.5 | 4 |
| 18.9 | 4 |
| 19.3 | 4 |
| 20.2 | 5 |
| 20.8 | 7 |
| 21.2 | 8 |
| 21.7 | 22 |
| 22.7 | 12 |
| 23.3 | 6 |
| 23.9 | 6 |
| 24.1 | 7 |
| 24.8 | 5 |
| 25.6 | 8 |
| 26.3 | 9 |
| 26.6 | 5 |
| 26.9 | 5 |
| 27.5 | 4 |
| 27.7 | 4 |
| 28.8 | 6 |
| 29.1 | 9 |
| 29.7 | 4 |
| 29.9 | 5 |
| 30.7 | 5 |
| 33.1 | 6 |
| 33.9 | 4 |
| 34.5 | 4 |
| 35.6 | 5 |
| 36.6 | 7 |
| 37.2 | 4 |
| 38.1 | 7 |

Example 2

Obtaining Crystal of 3SL Sodium Salt 8.0-Hydrate

A sodium hydroxide aqueous solution was added to an aqueous solution containing 100 g of 3SL in terms of free form so that the pH was adjusted 6.81 and the volume was made up to 2,900 mL. The aqueous solution was concentrated to 125 mL and the resulting concentrate was used for the next step.

While maintaining 125 mL of the concentrated solution at 25° C., 1 g of the crystal of 3SL sodium salt n-hydrate obtained in Example 1 was added as a seed crystal. 62.5 mL of 100%-ethanol was added dropwise thereto over 10 hours to precipitate the crystal. The crystal slurry was stirred for 12 hours to grow by aging the crystal. Then, the crystal was collected by filtration, washed with a 90% ethanol aqueous solution, and dried with forced air at 25° C. to obtain 64.8 g of the crystal. In the measurement of purity by HPLC, it was confirmed that the obtained crystal had a 3SL purity of 97.3% (area %) or more.

From the powder X-ray diffraction results of the obtained crystal, diffraction angles of the peaks in which the relative intensity ratio (I/I$_0$) was 4 or more are shown in Table 2. In the table, "2θ" indicates the diffraction angle (2θ°), and "Relative Intensity" indicates the relative intensity ratio (I/I$_0$).

TABLE 2

| 2θ | Relative Intensity |
|---|---|
| 7.2 | 100 |
| 8.6 | 4 |
| 9.8 | 13 |
| 10.3 | 6 |
| 10.9 | 20 |
| 12.6 | 8 |
| 13.4 | 6 |
| 14.9 | 7 |
| 15.7 | 4 |
| 15.9 | 5 |
| 16.4 | 11 |
| 17.1 | 11 |
| 17.4 | 6 |
| 17.8 | 11 |
| 18.5 | 8 |
| 18.9 | 6 |
| 19.3 | 4 |
| 19.7 | 3 |
| 20.2 | 8 |
| 20.9 | 9 |
| 21.2 | 14 |
| 21.8 | 12 |
| 22.7 | 15 |
| 23.3 | 13 |
| 23.9 | 9 |
| 24.1 | 11 |
| 24.7 | 11 |
| 25.6 | 11 |
| 26.0 | 5 |
| 26.3 | 7 |
| 26.8 | 8 |
| 27.8 | 6 |
| 28.2 | 7 |
| 28.8 | 6 |
| 29.1 | 4 |
| 29.7 | 5 |
| 29.9 | 5 |
| 30.7 | 6 |
| 31.9 | 4 |
| 33.1 | 6 |
| 33.4 | 4 |
| 33.8 | 4 |
| 34.5 | 3 |
| 35.6 | 9 |
| 36.5 | 8 |
| 37.2 | 4 |
| 37.5 | 4 |
| 38.1 | 6 |
| 39.3 | 4 |
| 41.0 | 4 |
| 42.3 | 5 |
| 43.5 | 4 |
| 45.8 | 5 |

The content of sodium in the crystal was measured by atomic absorption spectrophotometry, and as a result, it was 3.54 wt % and substantially coincided with the theoretical value (3.50 wt %) of a monosodium salt. In addition, the amount of water contained in the crystal was measured by the Karl-Fisher method, and as a result, it was 17.0 wt %, and the crystal of 3SL sodium salt was found to be 3SL sodium salt 8.0-hydrate by comparison with the theoretical amount of water.

Various physical properties of the crystal obtained in Example 2 are shown in Table 3. As for the pH, an aqueous solution at 50 g/L as a crystal of 3SL sodium salt 8.0-hydrate was measured. The melting point was measured using Melting Point M-565 (manufactured by BUCHI Corporation) under a condition of 50° C. to 200° C. and 0.5° C./min according to the instruction book.

TABLE 3

| Water Content % | Sodium Content % | Melting Point ° C. | pH |
|---|---|---|---|
| 17.0 | 3.54 | 174.6 | 6.00 |

The hygroscopicity of the crystal of 3SL sodium salt 8.0-hydrate obtained in Example 2 and that of a 3SL sodium reagent (amorphous salt, manufactured by Carbosynth Limited) were compared under the following conditions.

Storage conditions: 30° C., relative humidity of 80% (apparatus: THE051FA, manufactured by Advantec Toyo Kaisha Ltd.)

Measurement method: After about 100 mg of a sample was weighed with a precision balance, the sample was packed in a glass container and stored under the above-mentioned conditions. Thereafter, the sample was weighed again, and the weight change ratio was calculated.

The results are shown in Table 4. Incidentally, the weight of the sample at each elapsed time was measured by assuming the weight of each sample at the start of the test to be 100%.

TABLE 4

| Elapsed Time (hours) | 0 | 0.5 | 2.5 | 8 |
|---|---|---|---|---|
| Weight of crystal (%) | 100.0 | 100.2 | 99.9 | 99.9 |
| Weight of amorphous (%) | 100.0 | 123.1 | 130.5 | 130.4 |

As shown in Table 4, the crystal of 3SL sodium salt 8.0-hydrate ("crystal" in Table 4) obtained in Example 2 showed almost no change in weight with lapse of time. On the contrary, the 3SL sodium reagent ("amorphous" in Table 4) showed increase in weight with lapse of time. From these facts, it was confirmed that the crystal of 3SL sodium salt 8.0-hydrate had lower hygroscopicity and higher storage stability than the 3SL sodium reagent.

In addition, the heating stability of the amorphous 3SL sodium (freeze-dried product) obtained in Reference Example 1 and the crystal of 3SL sodium salt 8.0-hydrate obtained in Example 2 were compared under the following conditions. The results are shown in Table 5.

Storage conditions: 50° C., relative humidity of 50% (adjusted with saturated sodium bromide solution)

Measurement method: About 5 g of a sample was weighed with a precision balance, the sample was packed in a glass container, and the amount of impurities (glucose, lactose, sialic acid) after heating was evaluated by HPLC ("%" in Table 5 represents "wt %").

TABLE 5

| | | Elapsed Days (days) | | |
|---|---|---|---|---|
| | | 0 | 2 | 4 |
| Glucose (%) | Freeze-dried product | 0.11 | 0.14 | 0.16 |
| | Crystal | 0.03 | 0.04 | 0.04 |
| Lactose (%) | Freeze-dried product | 0.02 | 0.03 | 0.07 |
| | Crystal | 0.01 | 0.01 | 0.02 |
| Sialic acid (%) | Freeze-dried product | 0.14 | 0.21 | 0.26 |
| | Crystal | 0.08 | 0.10 | 0.09 |

As shown in Table 5, it was confirmed that the crystal of 3SL sodium salt 8.0-hydrate obtained in Example 2 ("Crystal" in Table 5) exhibits a small of increase in amount of impurities after heating and excellent heat stability, as compared with the amorphous 3SL sodium salt ("Freeze-dried product" in Table 5) obtained in Reference Example 1.

Example 3

Obtaining Crystal of 3SL Sodium Salt 2.0-Hydrate 50 g of 3SL sodium salt 8.0-hydrate obtained according to Example 2 was dried with forced air at 50° C. for 24 hours to obtain 43.3 g of a crystal. In the measurement of purity by HPLC, it was confirmed that the obtained crystal had a 3SL purity of 96.6% (area %) or more.

From the powder X-ray diffraction results of the crystal, diffraction angles of the peaks in which the relative intensity ratio ($I/I_0$) was 10 or more are shown in Table 6. In the table, "$2\theta$" indicates the diffraction angle ($2\theta°$), and "Relative Intensity" indicates the relative intensity ratio ($I/I_0$).

TABLE 6

| $2\theta$ | Relative Intensity |
|---|---|
| 8.9 | 100 |
| 10.8 | 16 |
| 11.8 | 18 |
| 13.3 | 22 |
| 15.5 | 31 |
| 17.1 | 32 |
| 17.9 | 16 |
| 18.7 | 15 |
| 19.3 | 28 |
| 20.0 | 16 |
| 20.9 | 28 |
| 21.8 | 16 |
| 22.5 | 19 |
| 23.7 | 17 |
| 25.0 | 17 |
| 25.9 | 13 |
| 27.4 | 24 |
| 28.5 | 15 |
| 32.8 | 12 |

As shown in Table 6, it was found that the powder X-ray diffraction pattern of the obtained crystal is different from the powder X-ray diffraction pattern of the crystal obtained according to Example 2, and the crystal was in a polymorphic relationship with the crystal obtained according to Example 2. The amount of water contained in the crystal was measured by the Karl-Fisher method, and as a result, it was 5.1 wt %, and the crystal of 3SL sodium salt was found to be 3SL sodium salt 2.0-hydrate by comparison with the theoretical amount of water.

Example 4

Single Crystal X-Ray Structure Analysis of 3SL Sodium Salt 8.0-Hydrate

In order to determine the structure of the crystal of 3SL sodium salt obtained in Example 2, single crystal X-ray diffraction (SXRD) was carried out using a measuring device (a single crystal X-ray structure analyzer R-AXIS RAPID-F, manufactured by Rigaku Corporation).

First, a single crystal of 3SL sodium salt was placed on a diffractometer, and a diffraction image was measured using an X-ray with a predetermined wavelength in the air at room temperature or in an inert gas stream at a predetermined temperature. Subsequently, from a set of a Miller index calculated from the diffraction image and a diffraction intensity, structure determination by a direct method and structure refinement [Acta Cryst. A64, 112 (2008)] by a least-squares method were performed, whereby a single crystal structure was obtained. The results are shown in Table 7.

TABLE 7

Crystal data

| | |
|---|---|
| Chemical Formula | Na$^+$•(C$_{23}$H$_{38}$NO$_{19}$)$^-$•8H$_2$O |
| M$_r$ | 799.66 |
| Crystal System, space group | Orthorhombic, P2$_1$2$_1$2$_1$ |
| Temperature (K) | 300 |
| a, b, c (Å) | 11.2942(5), 13.3269(6), 24.4525(12) |
| V (Å$^3$) | 3680.5(3) |
| Z | 4 |
| Radiation type | Cu Kα |
| μ (mm$^{-1}$) | 1.27 |
| Crystal size (mm) | 0.22 × 0.20 × 0.02 |
| Data collection | |
| Diffractometer | Rigaku R-AXIS RAPID-F |
| Absorption correction | Numerical |
| No. of measured, independent and observed [I > 2σ(I)] reflections | 65798, 6729, 4058 |
| R$_{int}$ | 0.0922 |
| (sin θ/λ)$_{max}$ (Å$^{-1}$) | 0.602 |
| Refinement | |
| R[F$^2$ > 2σ(F$^2$)], wR(F$^2$), S | 0.0598, 0.1291, 1.005 |
| No. of reflections | 6729 |
| No. of parameters | 543 |
| H-atom treatment | H-atom parameters constrained |
| Δρ$_{max}$, Δρ$_{min}$ (e Å$^{-3}$) | 0.21, −0.18 |
| Absolute structure | Flack x determined using 2949 Friedel pairs (Flack, 1983) |
| Absolute structure parameter | −0.02(14) |

Computer programs: RAPID AUTO (Rigaku, 2015), CrystalStructure (Rigaku, 2015), Superflp (Palatinus & Chapuis, 2007), SHELXL-97 (Sheldrick, 2008), Mercury (Macrae et al., 2008).
References
Flack, H. D. (1983). Acta Cryst. A39. 876-881.
Macrae, C. F., Bruno, I. J., Chisholm, J. A., Edgington, P. R., McCabe. P., Pidcock, E., Rodriguez-Monge, L., Taylor, R., van de Streek, J., Wood, P. A. (2008). *J. Appl. Cryst.* 41, 466-470.
Sheldrick, G. M. (2008). *Acta Cryst.* A64, 112-122.
Palatinus L., Chapuis G. (2007), *J. Appl. Cryst.* 40, 786-790.

As a result of the single crystal X-ray structure analysis, it was confirmed that the crystal was a crystal of 3SL sodium salt, and is a 3SL sodium salt 8.0-hydrate having 8 water molecules corresponding to 3SL molecule.

Example 5

Obtaining Crystal of 3SL Sodium Salt 5.0-Hydrate

The crystal of 3SL sodium salt 8.0-hydrate obtained in Example 2 was left to stand for 20 hours under a condition of 50° C. and dried. The amount of water contained in the crystal after drying was measured by the Karl-Fisher method, and as a result, it was 12.1 wt %, and the crystal of 3SL sodium salt was found to be 3SL sodium salt 5.0-hydrate by comparison with the theoretical amount of water.

The pattern of powder X-ray diffraction of the crystal was the same as the pattern of powder X-ray diffraction of the crystal obtained in Example 2. Thus, it was found that the crystal was the same polymorph as the crystal of 3SL sodium salt 8.0-hydrate.

From the results of Example 2 and Example 5, it was confirmed that, for the crystal of 3SL sodium salt n-hydrate, in the crystal of 8.0-hydrate and the crystal of 5.0-hydrate, the number of hydrates varied without involving changes in powder X-ray diffraction pattern. From this, it was considered that the 3SL sodium salt is a clathrate hydrate (J. Pharm. Sci., 64 (8), 1269 to 1288, 1975) whose number of hydrates varies without involving a structural change of the crystal cell. It is also recognized, for example, in WO 2014/069625 that a sugar compound forms a clathrate hydrate.

Therefore, it was found that the same crystalline state of n-hydrate which continues at least from 5.0-hydrate to 8.0-hydrate exists in the crystal of 3SL sodium salt n-hydrate.

Example 6

Obtaining Crystal of 3SL Sodium Salt 3.5-Hydrate

The crystal of 3SL sodium salt 8.0-hydrate obtained in Example 2 was dried with forced air under a condition of 45° C. for 20 hours. The amount of water contained in the crystal after drying was measured by the Karl-Fisher method, and as a result, it was 8.7 wt %, and the crystal of 3SL sodium salt was found to be 3SL sodium salt 3.5-hydrate by comparison with the theoretical amount of water.

The pattern of powder X-ray diffraction of the crystal was the same as the pattern of powder X-ray diffraction of the crystal obtained in Example 3. Thus, it was found that the crystal was the same polymorph as the crystal of 3SL sodium salt 2.0-hydrate.

Example 7

Obtaining Crystal of 3SL Sodium Salt 1.4-Hydrate

The crystal of 3SL sodium salt 8.0-hydrate obtained in Example 2 was vacuum-dried under a condition of 30° C. and 35 hPa for 56 hours.

The amount of water contained in the crystal after drying was measured by the Karl-Fisher method, and as a result, it was 3.7 wt %, and the crystal of 3SL sodium salt was found to be 3SL sodium salt 1.4-hydrate by comparison with the theoretical amount of water.

The pattern of powder X-ray diffraction of the crystal was the same as the pattern of powder X-ray diffraction of the crystal obtained in Example 3. Thus, it was found that the crystal was the same polymorph as the crystal of 3SL sodium salt 2.0-hydrate.

From the results of Example 2, Example 6, and Example 7, in the same manner as described above, it was found that the same crystalline state of n-hydrate which is consecutive at least from 1.4-hydrate to 3.5-hydrate exists in the crystal of 3SL sodium salt n-hydrate.

While the present invention has been described in detail with reference to specific embodiments, it is apparent to those skilled in the art that various changes and modifications can be made without departing from the spirit and scope of the present invention. This application is based on a Japanese patent application (Japanese Patent Application No. 2016-093664) filed on May 9, 2016, the entire contents of which are incorporated herein by reference. Further, all references cited herein are incorporated herein by reference in their entirety.

INDUSTRIAL APPLICABILITY

According to the present invention, there are provided a crystal of 3SL sodium salt n-hydrate which is useful, for example, as a product, a raw material, an intermediate, or the like of health food, pharmaceuticals, cosmetics, and the like, and a process for producing the crystal.

The invention claimed is:
1. A crystal of 3'-sialyllactose (hereinafter, referred to as 3SL) sodium salt n-hydrate wherein n represents any number of 0 to 9, and when n is 0, it is referred to as 3SL sodium salt anhydrate, wherein, when n is any number of 4 to 9, the crystal has peaks at diffraction angles (2θ°) of 7.2±0.2°, 10.9±0.2°, 22.7±0.2°, 21.2±0.2°, and 9.8±0.2° in powder X-ray diffraction, and when n is any number which is equal to or greater than 0 and less than 4, the crystal has peaks at diffraction angles (2θ°) of 8.9±0.2°, 17.1±0.2°, 15.5±0.2°, 19.3±0.2°, and 20.9±0.2° in powder X-ray diffraction.

2. The crystal according to claim 1, wherein n is any number of 4 to 9.

3. The crystal according to claim 2, wherein n is 5.0 or 8.0.

4. The crystal according to claim 2, wherein the crystal further has peaks at diffraction angles (2θ°) of 23.3±0.2°, 21.8±0.2°, 17.1±0.2°, 17.8±0.2°, and 24.1±0.2° in powder X-ray diffraction.

5. The crystal according to claim 4, wherein the crystal further has peaks at diffraction angles (2θ°) of 24.7±0.2°, 16.4±0.2°, 25.6±0.2°, 20.9±0.2°, and 23.9±0.2° in powder X-ray diffraction.

6. The crystal according to claim 2, wherein the crystal has the following approximate cell parameters when measured at −173° C. in single crystal X-ray structure analysis: a=11.2942 Å; b=13.3269 Å; c=24.4525 Å; V=3680.5 Å$^3$; and Z=4, and has a space group of $P2_12_12_1$.

7. The crystal according to claim 1, wherein n is any number which is equal to or greater than 0 and less than 4.

8. The crystal according to claim 7, wherein n is 1.4, 2.0, or 3.5.

9. The crystal according to claim 7, wherein the crystal further has peaks at diffraction angles (2θ°) of 27.4±0.2°, 13.3±0.2°, 22.5±0.2°, 11.8±0.2°, and 23.7±0.2° in powder X-ray diffraction.

10. The crystal according to claim 9, wherein the crystal further has peaks at diffraction angles (2θ°) of 25.0±0.2°, 10.8±0.2°, 17.9±0.2°, 20.0±0.2°, and 21.8±0.2° in powder X-ray diffraction.

11. A process for producing the crystal according to claim 2, comprising a step of precipitating a crystal of 3SL sodium salt n-hydrate by causing a 3SL aqueous solution containing a sodium-containing compound to be left to stand or to be stirred, and a step of collecting the crystal of 3SL sodium salt n-hydrate from the aqueous solution.

12. A process for producing the crystal according to claim 2, comprising a step of adding a crystal of 3SL sodium salt n-hydrate as a seed crystal to a 3SL aqueous solution containing a sodium-containing compound, a step of precipitating a crystal of 3SL sodium salt n-hydrate in the aqueous solution, and a step of collecting the crystal of 3SL sodium salt n-hydrate from the aqueous solution.

13. The process according to claim 12, wherein the step of precipitating the crystal of 3SL sodium salt n-hydrate is a step of precipitating a crystal of 3SL sodium salt n-hydrate by adding or adding dropwise an alcohol solution to the aqueous solution.

14. The process according to claim 13, wherein the alcohol solution is a solution selected from the group consisting of C1 to C6 alcohols.

15. A process for producing the crystal according to claim 7, comprising a step of performing forced air drying of a crystal of 3'-sialyllactose sodium salt n-hydrate, wherein n is any number of 4 to 9, at 45° C. or more for 20 hours or more, or a step of performing vacuum drying of the same at 25° C. or more for 48 hours or more.

\* \* \* \* \*

UNITED STATES PATENT AND TRADEMARK OFFICE
CERTIFICATE OF CORRECTION

PATENT NO. : 11,008,355 B2
APPLICATION NO. : 16/099877
DATED : May 18, 2021
INVENTOR(S) : Yokoi et al.

It is certified that error appears in the above-identified patent and that said Letters Patent is hereby corrected as shown below:

In the Claims

Claim 6, Column 19, Line 24, "a=11.2942 A; b=13.3269 A; c=24.4525 A; V=3680.5 A$^3$;" should read "a=11.2942 Å; b = 13.3269 Å; c = 24.4525 Å; V = 3680.5 Å$^3$;"

Signed and Sealed this
Ninth Day of November, 2021

Drew Hirshfeld
*Performing the Functions and Duties of the
Under Secretary of Commerce for Intellectual Property and
Director of the United States Patent and Trademark Office*